(12) United States Patent
Mikekado et al.

(10) Patent No.: US 9,012,521 B2
(45) Date of Patent: Apr. 21, 2015

(54) PYRROLOQUINOLINE QUINONE GEL

(75) Inventors: Tsuyoshi Mikekado, Niigata (JP); Kazuto Ikemoto, Niigata (JP); Hajime Shimizu, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/814,820

(22) PCT Filed: Aug. 9, 2011

(86) PCT No.: PCT/JP2011/068181
§ 371 (c)(1),
(2), (4) Date: Apr. 16, 2013

(87) PCT Pub. No.: WO2012/020767
PCT Pub. Date: Feb. 16, 2012

(65) Prior Publication Data
US 2013/0203869 A1     Aug. 8, 2013

(30) Foreign Application Priority Data

Aug. 9, 2010  (JP) ................................ 2010-178349

(51) Int. Cl.
| | | |
|---|---|---|
| *A61K 8/02* | (2006.01) | |
| *A23L 1/054* | (2006.01) | |
| *A23L 1/05* | (2006.01) | |
| *A61Q 19/00* | (2006.01) | |
| *A61K 8/04* | (2006.01) | |
| *A61K 31/4745* | (2006.01) | |
| *A61K 9/06* | (2006.01) | |
| *A23L 1/30* | (2006.01) | |
| *A61K 8/49* | (2006.01) | |
| *A61P 3/02* | (2006.01) | |
| *A61P 43/00* | (2006.01) | |

(52) U.S. Cl.
CPC . *A23L 1/054* (2013.01); *A23L 1/05* (2013.01); *A61K 8/042* (2013.01); *A61K 31/4745* (2013.01); *A61K 2800/48* (2013.01); *A61Q 19/00* (2013.01); *A61K 9/06* (2013.01); *A23L 1/30* (2013.01); *A61K 8/494* (2013.01); *A61K 8/0216* (2013.01); *A61K 2800/84* (2013.01); *Y10S 514/944* (2013.01)

(58) Field of Classification Search
CPC .......... A61Q 19/00; A61K 8/042; A23L 1/05; A23L 1/054; A23L 1/0014
See application file for complete search history.

(56) References Cited

U.S. PATENT DOCUMENTS

| | | | |
|---|---|---|---|
| 2007/0053849 A1* | 3/2007 | Doyle et al. .................... 424/50 |
| 2007/0065488 A1* | 3/2007 | Ishizaki et al. ................ 424/439 |
| 2007/0196349 A1* | 8/2007 | Kitamura et al. ............ 424/94.1 |
| 2007/0259908 A1 | 11/2007 | Fujii et al. |
| 2007/0293572 A1* | 12/2007 | Kishida et al. ................ 514/561 |
| 2008/0152706 A1 | 6/2008 | Shi et al. |
| 2009/0191320 A1* | 7/2009 | Gu et al. ..................... 426/330.1 |
| 2010/0233328 A1* | 9/2010 | Ferrell .......................... 426/124 |

FOREIGN PATENT DOCUMENTS

| | | |
|---|---|---|
| CN | 101507724 A * | 8/2009 |
| JP | 59 113896 | 6/1984 |
| JP | 1-218597 A | 8/1989 |
| JP | 2692167 B2 | 12/1997 |
| JP | 2009 185228 | 8/2009 |
| WO | 2006 025247 | 3/2006 |
| WO | 2008 023277 | 2/2008 |
| WO | WO 2009136587 A1 * | 11/2009 |

OTHER PUBLICATIONS

English translation of WO 2009136587 A1 obtained from Google translation on Apr. 18, 2014.*
English translation of CN 1001507724 A obtained from ProQuest Dialog on Apr. 18, 2014.*
Brief Communications, Nutritional Biochemistry, "A New Redox-cofactor Vitamin for Mammals", Nature, vol. 422, Apr. 24, 2003, p. 832.
E. J. Corey et al., "Total Synthesis of the Quinonoid Alcohol Dehydrogenase Coenzyme (1) of Methylotrophic Bacteria", JACS, vol. 103, 1981, pp. 5599-5600.
Toshimasa Ishida et al., "Molecular and Crystal Structure of PQQ (Methoxatin), a Novel Coenzyme of Quinoproteins: Extensive Stacking Character and Metal Ion Interaction", JACS, vol. 111, 1989, pp. 6822-6828.
Lara A. Estroff et al., "Effective Gelation of Water Using a Series of Bis-urea Dicarboxylic Acids", Angew. Chem. Int. Ed, vol. 39, No. 19, 2000, pp. 3447-3450.
Menger, F., et al., "Anatomy of Gel. Amino Acid Derivatives That Rigidify Water at Submillimolar Concentrations," J. Am. Chem. Soc., vol. 122, pp. 11679-11691, (2000).
International Search Report Issued Nov. 15, 2011 in PCT/JP11/068181 Filed Agusut 9, 2011.

* cited by examiner

*Primary Examiner* — Robert T Crow
*Assistant Examiner* — John P Nguyen
(74) *Attorney, Agent, or Firm* — Oblon, McClelland, Maier & Neustadt, L.L.P.

(57) ABSTRACT

An object of the present invention is to provide a gel containing pyrroloquinoline quinone that is capable of easily forming a gel near room temperature and is useful even in the food sector, and a method for producing the gel. According to the present invention, there is provided a gel containing pyrroloquinoline quinone that uses pyrroloquinoline quinone itself as a gelling agent and a method for producing the gel by adding a salt of pyrroloquinoline quinone to water and subsequently adjusting the temperature or the pH to reduce solubility.

20 Claims, 9 Drawing Sheets

PYRROLOQUINOLINE QUINONE GEL

CROSS-REFERENCE TO RELATED APPLICATION

This application is a 371 of PCT/JP2011/068181, filed Aug. 9, 2011.

This application enjoys the benefit of Japanese Patent Application No. 2010-178349, filed on Aug. 9, 2010. The disclosure of this earlier application is incorporated herein by reference in its entirety.

TECHNICAL FIELD

This invention relates to a gel containing pyrroloquinoline quinone and a method for producing the gel.

BACKGROUND ART

Pyrroloquinoline quinone (hereinafter sometimes referred to as "PQQ") has been proposed as a possible new vitamin (Non-patent document 1), and has attracted much attention as a useful material for dietary supplements, cosmetics, etc. Moreover, PQQ is present not only in bacteria but also in eukaryotic molds and yeasts and plays an important role as a coenzyme. Also, PQQ has been found to have many physiological activities such as cell growth-promoting activity, anti-cataract activity, hepatic disease-preventing and therapeutic activity, wound healing activity, antiallergic activity, reverse transcriptase-inhibiting activity, glyoxalase I-inhibiting activity-anticancer activity, and the like.

PQQ can be obtained by subjecting PQQ crude product obtained by methodologies such as organic chemical syntheses (Non-patent document 2) and fermentation processes (Patent document 1) to chromatography and concentrating the PQQ fraction in the effluent to crystallize PQQ by crystallization, followed by drying the crystallized PQQ (Patent document 2). The crystal structure of this PQQ salt has been reported (Non-patent document 3).

Heretofore, foods and pharmaceuticals containing PQQ have often been provided in solution or powder. Gel-like substances containing PQQ are not known. Gelled foods and pharmaceuticals, which are different in the tactile sense and handling from liquid ones, are widely used such as jellies and puddings. Moreover, use of jelly-like foods and pharmaceuticals are to be desired because they are easily swallowed even for those with impaired swallowing function (difficulty swallowing food) due to aging and diseases who find it difficult to take hard tablets. In addition to the food sector, and for cosmetics and chromatography, gel-like substances are also used for familiar goods such as athletic shoes and deodorants.

Usually, gelling agents used in the food and pharmaceutical sectors are macromolecular substances represented by collagen, hyaluronic acid, vegetable gelatin and carrageenan. Besides such macromolecular compounds, some small molecule compounds are reported to form a gel as gelling agents (Non-patent documents 4 and 5). However, no small molecule gelling agents are known that can be used for food products. Furthermore, gelling agents for use in the food sector are required to form a gel at near room temperature for preventing denaturation, although many of the macromolecular gelling agents are often formed by dissolving by warming and then cooling.

PRIOR ART DOCUMENTS

Patent Document

Patent document 1: Japanese Patent Application Laid-Open Publication NO. 1-218597
Patent document 2: Japanese Patent NO. 2692167

Non-Patent Document

Non-patent document 1: Nature, vol. 422, 24 April, 3003, pp 832
Non-patent document 2: JACS, vol. 103, pp. 5599-5600 (1981)
Non-patent document 3: JACS, vol. 111, pp. 6822-6828 (1989)
Non-patent document 4 JACS, vol. 122, pp. 11679-11691 (2000)
Non-patent document 5: Angew. Chem. Int. Ed, vol. 39, pp. 3447-3450 (2000)

SUMMARY OF THE INVENTION

Problem to be Solved by the Invention

The present inventors have found that a gel comprising a salt of pyrroloquinoline quinone formed into a fibrous structure is obtained by mixing the salt of pyrroloquinoline quinone with a dispersion medium at room temperature and decreasing the temperature of the resulting mixture by 10° C. or more. According to the present invention, the salt of pyrroloquinoline quinone can form into a gel without dissolving in a dispersion medium (solvent) under predetermined conditions. The present invention is based on this finding.

The present invention provides a gel containing pyrroloquinoline quinone that is capable of easily forming a gel near room temperature and is usable even in the food sector, and a method for producing the gel.

Means for Solving Problem

According to the present invention, the following inventions are provided:

(1) a gel comprising a salt of pyrroloquinoline quinone;
(2) the gel of (1), characterized by that the salts of pyrroloquinoline quinone are associated with each other to form a fibrous structure;
(3) the gel of (1) or (2), wherein the salt of pyrroloquinoline quinone is present in an amount of 0.5 to 70% by weight based on the total weight of the gel;
(4) the gel of any one of (1) to (3), wherein the salt is sodium salt;
(5) the gel of any one of (1) to (4), which is produced by decreasing the solubility of the salt of pyrroloquinoline quinone in a mixture of the salt of pyrroloquinoline quinone and the dispersion medium;
(6) the gel of (5), wherein the decrease in the solubility in the mixture is performed by decreasing the temperature of the mixture by 10° C. or more;
(7) the gel of (5), wherein the decrease in the solubility in the mixture is performed by decreasing the pH of the mixture by 0.1 or more;
(8) the gel of any one of (1)-(7), further comprising a sweetener;
(9) the gel of any one of (1)-(8), further comprising a macromolecular gelling agent;
(10) A dried product of the gel of any one of (1)-(9);
(11) a fibrous structure consisting of a salt of pyrroloquinoline quinone;
(12) a food product comprising the gel of any one of (1)-(9), the dried product of (10) or the fibrous structure of (11);

(13) a pharmaceutical product comprising the gel of any one of (1)-(9), the dried product of (10) or the fibrous structure of (11);
(14) a cosmetic comprising the gel of any one of (1)-(9), the dried product of (10) or the fibrous structure of (11);
(15) a gelling agent comprising a salt of pyrroloquinoline quinone;
(16) a method for producing a gel comprising a salt of pyrroloquinoline quinone, comprising decreasing the solubility of the salt of pyrroloquinoline quinone in a mixture of the salt of pyrroloquinoline quinone and a dispersion medium;
(17) the method of (16), wherein the decrease in the solubility in the mixture is performed by decreasing the temperature of the resulting mixture by 10° C. or more;
(18) the method of (16), wherein the decrease in the solubility in the mixture is performed by decreasing the pH of the mixture by 0.1 or more.

The gel of the present invention is a novel edible small molecule gel. The present invention can provide a hydrated gel containing PQQ. Advantageously, according to the present invention, no warming process is required because gelation can be carried out at room temperature or lower. Also advantageously, according to the present invention, there is provided a PQQ-containing liquid which becomes homogeneous even in high concentrations through gelation. Moreover, advantageously, according to the present invention, this gel can be used for food products, functional food products, pharmaceutical products, quasi drugs, cosmetics and the like because the dissolution rate of the gel is different from that of crystals in the same amount as the gel so that the solubility can be controlled.

DETAILED DESCRIPTION OF THE INVENTION

Figure 1:
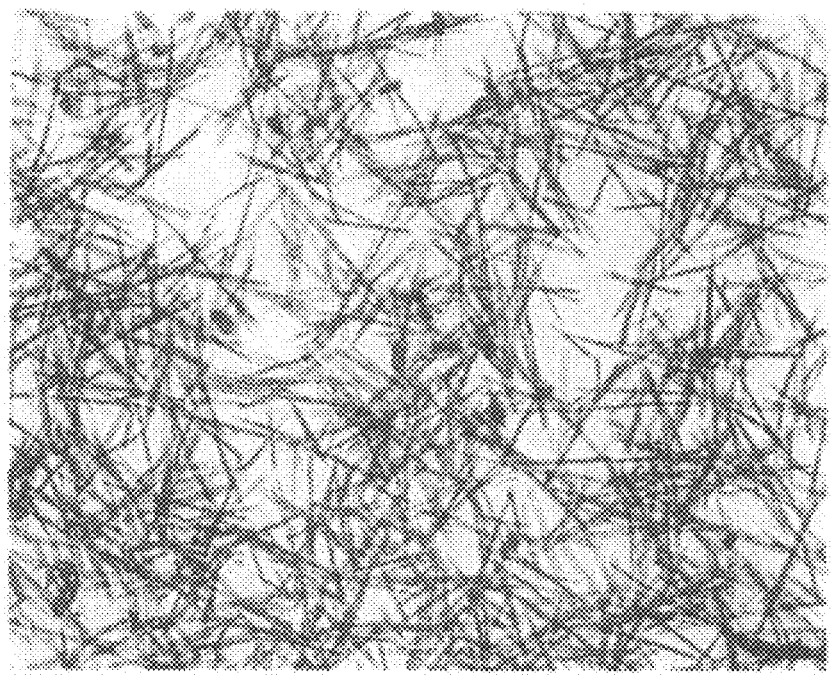
FIG. 1 shows an optical micrograph of a raw material PQQ disodium salt crystal.

According to the present invention, a gel comprising a salt of pyrroloquinoline quinone can be produced by decreasing the solubility of the salt of pyrroloquinoline quinone in a mixture of the salt of pyrroloquinoline quinone and a dispersion medium.

The "gel comprising a salt of pyrroloquinoline quinone" is a gel consisting substantially of a salt of pyrroloquinoline quinone and a dispersion medium. In the gel of the present invention, the salts of pyrroloquinoline quinone are associated with each other to form a fibrous structure within which the dispersion medium is included.

The "fibrous structure" as used herein refers to a three-dimensional network structure formed by self-association of the salts of pyrroloquinoline quinone via interactions other than covalent bond to form an association thereof and physically cross-linking the association. That is, the gel of the present invention can be a physical gel. The interactions other than covalent bonds include non-covalent bonds such as hydrogen bonds, ionic bonds, coordination bonds, n-n interactions (stacking), hydrophobic interactions and the like, and they are hydrogen bonds and ionic bonds in particular.

The salt of pyrroloquinoline quinone used in the present invention is a salt having the structural formula represented by the following formula (1):

[Compound 1]

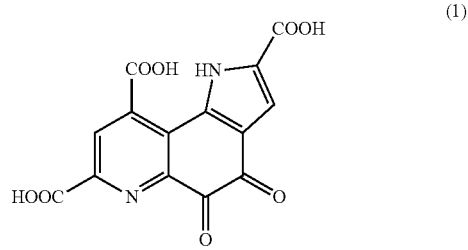

(1)

The salt of pyrroloquinoline quinone used in the present invention includes an alkali metal salt, an alkaline earth metal salt, an ammonium salt of pyrroloquinoline quinone, with alkali metal salt being preferred. The salt of pyrroloquinoline quinone may be used alone or in a mixture.

The alkali metal salt of pyrroloquinoline quinone used in the present invention includes salts of sodium, potassium, Lithium, Calcium, Magnesium, cesium, rubidium, and the like. Preferred is the sodium salt. Pyrroloquinoline quinone may be substituted with one to three atoms of alkali metals to form an alkali metal salt thereof, which may be any of a monoalkali metal salt, a dialkali metal salt and a trialkali metal salt, preferably a dialkali metal salt. The alkali metal salt of pyrroloquinoline quinone is especially preferably the disodium salt.

To obtain a gel with better reproducibility, the salt of pyrroloquinoline quinone in a form of crystal can be used. As a raw material used, preferred is the disodium salt in a needle-like crystalline form having a crystal structure represented by peaks at 2θ of 9.1, 10.3, 13.8±0.4° in the powder X-ray diffraction using Cu Kα radiation.

When the salt of pyrroloquinoline quinone in a crystalline form is used, the salt can have a degree of crystallinity of 0 to 100% and preferably 20-100%.

The salt of pyrroloquinoline quinone used in the present invention can be commercially available or produced by known methods.

According to Examples described later, the present invention is characterized by achieving gel formation of PQQ itself from the salt of PQQ and the dispersion medium (water), and the gel can be produced without any common gelling agent.

Generally, the gel formation takes place by fiber polymer chains expanding through the solution to hold the liquid. Well known examples are vegetable gelatin and collagen, and polymer chains thereof hold water.

PQQ is a small molecule and is first required to become fibrous for gel formation. PQQ is thought to be fibered by the molecule chains expanding via non-covalent bond formation. While this gelation using the non-covalent bond formation easily varies depending on the conditions such as the concentration of the salt, precursors thereof, the temperature and the like, the gel of the present invention can be produced as follows:

A gel comprising a salt of pyrroloquinoline quinone can be produced by mixing the salt of pyrroloquinoline quinone with a dispersion medium and decreasing the solubility of the salt of pyrroloquinoline quinone in the resulting mixture. To decrease the solubility of the salt of pyrroloquinoline quinone, the temperature or pH of the mixture can be adjusted. Specifically, a gel having a fibrous structure formed by the association of the salts of pyrroloquinoline quinone with each other can be produced by mixing the salt of pyrroloquinoline quinone with the dispersion medium and decreasing the temperature of the resulting mixture by 10° C. or more. Alternatively, a gel having a fibrous structure formed by association of the salts of pyrroloquinoline quinone with each other can be produced by mixing the salt of pyrroloquinoline quinone with the dispersion medium and decreasing the pH of the resulting mixture by 2 or more.

If this fibrous structure can be held, then a gel that is a solid including the solvent is formed. Although gelation typically takes places in water in the present invention, the water included within this gel may be substituted with other liquids. The water may be substituted with ethanol, propanol, butanol, and fat and oil as a liquid. The present invention can be not only a hydrated gel but also a gel containing an organic solvent.

That is, the dispersion medium used in the present invention includes water, organic solvents (for example, ethanol, propanol, butanol, glycerin, propylene glycol), fat and oil, and the like with water being preferred. When the dispersion medium is water, a hydrated gel (hydrogel) can be formed.

When mixing the salt of pyrroloquinoline quinone with the dispersion medium, the salt of pyrroloquinoline quinone may be added to the dispersion medium, the dispersion medium may be added to the salt of pyrroloquinoline quinone, or the salt of pyrroloquinoline quinone and the disperse medium may be added into separate vessels. Preferably, the salt of pyrroloquinoline quinone can be added to the dispersion medium. Preferably, the concentration of the salt of pyrroloquinoline quinone here is the same or higher than the solubility. The "solubility" as used herein refers to the extent to which a solute dissolves in a solvent, and can be expressed by the concentration of the solute in the saturated solution. The solubility of the salt of pyrroloquinoline quinone can be suitably determined by the temperature of the mixture. For instance, the solubility of pyrroloquinoline quinone disodium in water at 25° C. is 0.299 g per 100 g of water.

The weight concentration of the salt of pyrroloquinoline quinone in the mixture is preferably 0.5 to 70% by weight, and more preferably 0.7 to 20% by weight. In the mixture with a lower concentration of the salt of pyrroloquinoline quinone, the salt is dissolved, for example, in pure water, and gelation does not take place. On the other hand, the mixture with a higher concentration of the salt of pyrroloquinoline quinone becomes clay-like, which makes it difficult to determine whether the gel state is formed. To increase the PQQ content, once gelation takes place, the solid salt of PQQ can be added to form a gel having a higher concentration of the gel. The weight concentration of the salt of pyrroloquinoline quinone is preferably 0.7 to 20% by weight and more preferably 0.7 to 10% by weight in the mixture at a temperature of 20 to 50° C.

When the temperature of the mixture is adjusted for decreasing the solubility of the salt of pyrroloquinoline quinone, the salt of pyrroloquinoline quinone can be mixed with the disperse medium at temperature from −30 to 150° C. Preferably, under conditions where the mixture is partially dissolved at room temperature or higher, i.e. 20 to 100° C., the original crystals of the salt dissolve to facilitate structural conversion. More preferably, the temperature of the mixture can be 20 to 50° C., further preferably 20 to 40° C., and furthermore preferably 20 to 30° C.

The resulting mixture can have a pH of 2 to 10.

The resulting mixture may be stirred. The stirring can be accomplished by subjecting the mixture to magnetic stirring, mechanical stirring, manual stirring, and shake stirring, and preferably, mechanical stirring, manual stirring, and shake stirring.

To decrease the solubility of the salt of pyrroloquinoline quinone, the temperature of the resulting mixture can be −20 to 100° C., and more preferably −10 to 50° C. When the mixture is at a higher temperature, the solubility of PQQ increases, which increases the amount of PQQ necessary to form fibers for gelation. On the other hand, when the temperature of the mixture is too low, the solubility of PQQ becomes to low, which decreases the rate of the structural conversion necessary for forming fibrous solids. Also, water freezes so that gelation does not take place.

That is, the temperature of the resulting mixture can be decreased by 10° C. or more, preferably by 15° C. or more, and more preferably by 20° C. or more from the original temperature. The temperature of the resulting mixture can be also decreased by 10 to 120° C. and preferably 15 to 50° C. from the original temperature. The temperature of the mixture can be, for example, −20 to 20° C., preferably −15 to 15° C., and more preferably −10 to 10° C. This decreases the solubility to form fibrous solids, resulting in gelation. Any technique can be used for decreasing the temperature of the mixture. For example, the mixture can be placed in the refrigerator to decrease the temperature of the mixture.

When the temperature of the mixture is decreased, the mixture may be stirred. The stirring can be accomplished by subjecting the mixture to magnetic stirring, mechanical stirring, manual stirring, and shake stirring, and preferably, mechanical stirring, manual stirring, and shake stirring.

When the temperature of the mixture is decreased, the mixture can be allowed to stand still. The period of standing still can be 0.5 minute to 2 weeks, and preferably 30 minutes to 1 week.

When the pH of the mixture is adjusted for decreasing the solubility of the salt of pyrroloquinoline quinone, the salt of pyrroloquinoline quinone can be mixed with the dispersion medium at pH 2 to 10.

The temperature of the resulting mixture can be −30 to 150° C., and preferably 20 to 100° C.

The resulting mixture may be stirred. The stirring can be accomplished by subjecting the mixture to magnetic stirring, mechanical stirring, manual stirring, and shake stirring, and preferably, mechanical stirring, manual stirring, and shake stirring.

To decrease the solubility of the salt of pyrroloquinoline quinone, the resulting mixture can have a pH of 2 to 4. That is, the pH of the resulting mixture can be decreased by 0.1 or more, preferably 0.2 or more, and more preferably 0.3 or more from the original pH. The solubility of the salt of pyrroloquinoline quinone can be decreased by changing the pH of the mixture (in particular, changing the pH range from the range of 6 to 10 to the range of 2 to 4), and therefore, the gel of the present invention can be produced. Any technique can be used for decreasing the pH of the mixture. For example, the pH of the mixture can be adjusted using an acidic substance (for example, hydrochloric acid) and an alkaline substance (for example, sodium hydroxide).

When the pH of the mixture is decreased, the mixture may be stirred. The stirring can be accomplished by subjecting the mixture to magnetic stirring, mechanical stirring, manual stirring, and shake stirring, and preferably, mechanical stirring, manual stirring, and shake stirring.

When the pH of the mixture is decreased, the mixture can be allowed to stand still. The period of standing still can be 0.5 minute to 2 weeks, and preferably 30 minutes to 1 week.

The gel of the present invention thus forms a fibrous structure with molecular linkage, wherein the formation of the structure proceeds at room temperature, and there is no need to warm for dissolving unlike gelling agents like conventional vegetable gelatins.

It is expected that ionic bonds with alkaline metals and hydrogen bonds are formed between the molecules of PQQ. When the PQQ concentration is high, a substance containing the original crystal structure in addition to the fibrous structure to be gelled is formed. However, there is no problem in particular as long as gel formation has taken place. Moreover, once gel formation has taken place, the resulting substance may be mixed with PQQ powder.

When PQQ molecules are to form the fibrous structure, the molecular chain is thought to be extended. The present inventors consider as follows: The crystal structure described in Non-patent document 3 shows that hydrogen bonds and ionic bonds are present between the molecules of the disodium salt of PQQ, and also stacking of aromatic rings is considered. It is considered that the PQQ formed into the fibrous structure has a structure distinct from that of the crystalline PQQ, but has a similar structure in short repeat units, and that the bonding between the molecules is therefore achieved via the above-mentioned interactions between the molecules. In the formula (2) below, some of the expected links between the molecules are described.

Specifically, it is considered that the molecules are associated via the following interactions:

the ionic bond between the nitrogen atom at the pyridine backbone of one pyrroloquinoline quinone and an oxygen atom of the carboxylic acid group of another pyrroloquinoline quinone via an alkaline metal;

the ionic bond between the nitrogen atom at the pyridine backbone of one pyrroloquinoline quinone and an oxygen atom of the quinone of another pyrroloquinoline quinone via an alkaline metal;

the hydrogen bond between the carboxylic acid of one pyrroloquinoline quinone and an oxygen atom of the carboxylic acid of another pyrroloquinoline quinone;

the n-n stacking of the aromatic rings of one pyrroloquinoline quinone and the aromatic rings of another pyrroloquinoline quinone.

The gel of the present invention has a weight concentration of 0.5 to 70% by weight, more preferably 0.7 to 20% by weight, and further preferably 0.7 to 10% by weight of the salt of pyrroloquinoline quinone based on the total weight of the gel.

The gel of the present invention has a lower dissolution rate compared to that of the original crystalline substance, and can therefore change the dissolution rate simply by carrying out gelation operations without adding a dissolution-controlling agent into PQQ. This is very effective as an advantage of inhibiting denaturation or as a technology of slowly releasing when the gel is mixed with other materials. It is assumed that this characteristic results from the arrangement of the molecules of PQQ having a poorly water-soluble structure when the fibrous structure is formed. The gel of the present invention can be used as a sustained-release substrate.

In the gel of the present invention, the dissolution rate can also be controlled by adjusting the pH. In the gel of the present invention, the dissolution can be inhibited under acidic conditions, and can be facilitated under neutral conditions.

According to a preferred embodiment of the present invention, there are provided a gel comprising a sodium salt of pyrroloquinoline quinone produced by decreasing the temperature of 20 to 40° C. of the mixture of a sodium salt of pyrroloquinoline quinone and a dispersion medium by 10° C. or more to −10 to 10° C., and a method for producing the gel. Here, the weight concentration of the sodium salt of pyrroloquinoline quinone in the mixture is preferably 0.7 to 20% by weight, and more preferably 0.7 to 10% by weight.

[Compound 2]

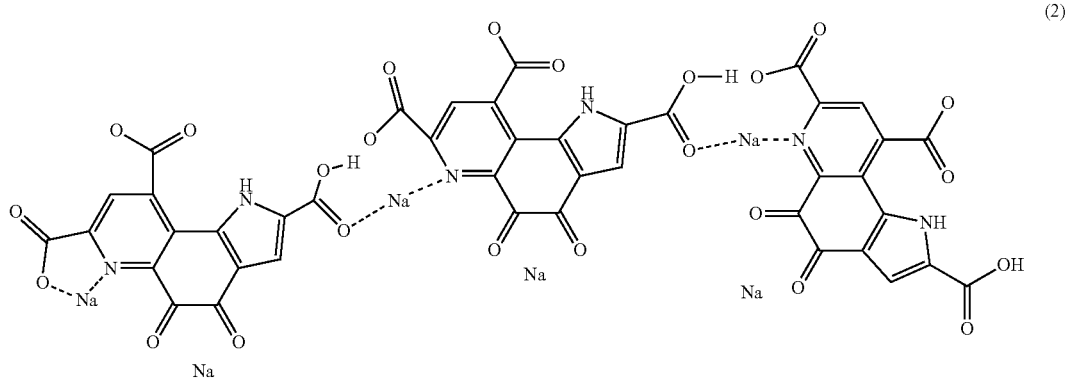

(2)

According to a more preferred embodiment of the present invention, there are provided a gel comprising a sodium salt of pyrroloquinoline quinone produced by decreasing the temperature of 20 to 40° C. of the mixture of a sodium salt of pyrroloquinoline quinone and a dispersion medium by 20° C. or more to −10 to 10° C., and a method for producing the gel. Here, the weight concentration of the sodium salt of pyrroloquinoline quinone in the mixture is preferably 0.7 to 20% by weight, and more preferably 0.7 to 10% by weight.

A fibrous structure (fibrous substance) consisting of the salt of PQQ can be produced by drying the gel of the present invention.

The fibrous structure of the present invention can be produced by drying the gel of the present invention by methods such as lyophilization, spray drying, and drying by heating after solvent displacement. The solid made by drying the gel is characterized by having a large surface area and being fibrous, resulting in a substance different in texture and appearance from common powders, which is important in the food, cosmetic, and pharmaceutical sectors. In addition, this may also be cast on a plate and made into film.

The fibrous structure of the present invention can have a fiber thickness of 0.02 to 2000 μm, preferably 0.05 to 500 μm, more preferably 0.05 to 50 μm and further more preferably 0.05 to 5 μm. In the present invention, the fiber thickness can be measured using a microscope (an electron microscope, an optical microscope, a probe and the like).

The gel of the present invention, which is edible, can also be mixed with sweeteners used for conventional gel-like food products. The gel can be mixed with a monosaccharide, a disaccharide, an oligosaccharide, and an artificial sweetener as a sweetener. Examples include fructose, glucose, galactose, sorbitol, xylitol, erythritol, trehalose, Palatinit, aspartame, acesulfame K, sucralose, glycyrrhiza extract, Lo Han Kuo starch syrup, honey, etc.

It is also possible to mix the gel with a conventional macromolecular gelling agent for improving the properties of the gel. Commonly used are gelatin, vegetable gelatin, carrageenan, collagen, fucoidan, hyaluronic acid, konnyaku, glucomannan, pectin, locust bean gum, xanthan gum, gellan gum, starch, egg white, etc. These may be mixed in a gelled state, or simultaneously formed into a gel.

Other components required to produce food products and cosmetic products can be added if necessary. Flavoring agent, acidulant, salt, umami component, fruit juice, fermented food, lipid, moisturizer, whitening agent, herbal extract, tea, coffee, emulsifier, glycerin, antiseptic agents, anti-microbial agent, steroid, methyl salicylate, vitamin, indometacin, etc. may be added if necessary.

When the mixture of these ingredients is formed, these ingredients are desirably added to such an extent that the gel of PQQ is not collapsed, and preferably mixed under conditions of room temperature or lower. Conditions under which PQQ is completely dissolved is not preferred. Under such conditions, there is a risk of separating out crystalline or amorphous PQQ without gelation.

For use in food, pharmaceutical, cosmetic applications, it is natural to be careful from a hygienic point of view, and the production is desirably done in an aseptic environment, for example, clean room.

According to the present invention, there can be provided a gelling agent comprising a salt of pyrroloquinoline quinone.

According to the present invention, the following inventions are also provided.

(1) A gel consisting of a salt of pyrroloquinoline quinone;
(2) the gel of (1), characterized by that the salt of pyrroloquinoline quinone is present in an amount of 0.5 to 70% by weight;
(3) the gel of (1) or (2), characterized by consisting of a sodium salt of pyrroloquinoline quinone;
(4) the gel of any one of (1) to (3), containing a sweetener;
(5) the gel of any one of (1) to (4), containing a macromolecular gelling agent;
(6) a fibrous substance consisting of a salt of pyrroloquinoline quinone;
(7) a method for producing a gel consisting of a salt of pyrroloquinoline quinone, characterized by adding the salt of pyrroloquinoline quinone to water, stirring the mixture at 20 to 100° C., and subsequently decreasing the temperature of the mixture by 10° C. or more or decreasing the pH of the mixture;
(8) a food product comprising the gel of any one of (1) to (5);
(9) a pharmaceutical product comprising the gel of any one of (1) to (5);
(10) a cosmetic product comprising the gel of any one of (1) to (5);
(11) a food product comprising the fibrous substance of (6);
(12) a pharmaceutical product comprising the fibrous substance of (6);
(13) a cosmetic product comprising the fibrous substance of (6).

EXAMPLES

The present invention will now be described more specifically with reference to the following examples and comparative examples, but is not intended to be limited thereto.

In Examples and Comparative Examples, powder X-ray diffraction (hereinafter described as XRD) was performed on a M18XCE manufactured by MAC Science Corporation, at Cu/tube voltage of 40 kV/tube current of 100 mA, divergence slit: 1°, scattering slit: 1°, receiving slit: 0.3 mm, scanning rate: 4.000°/min, and sampling width: 0.020°.

In Examples and Comparative Examples, optical micrographs were taken using a microscope TE-2000S manufactured by NIKON equipped with a ×40 objective lens.

In Examples and Comparative Examples, UV measurements were performed using a HITACHI U-2000 Spectrophotometer.

Comparative Example 1

A Raw Material Pyrroloquinoline Quinone Disodium

Figure 2:
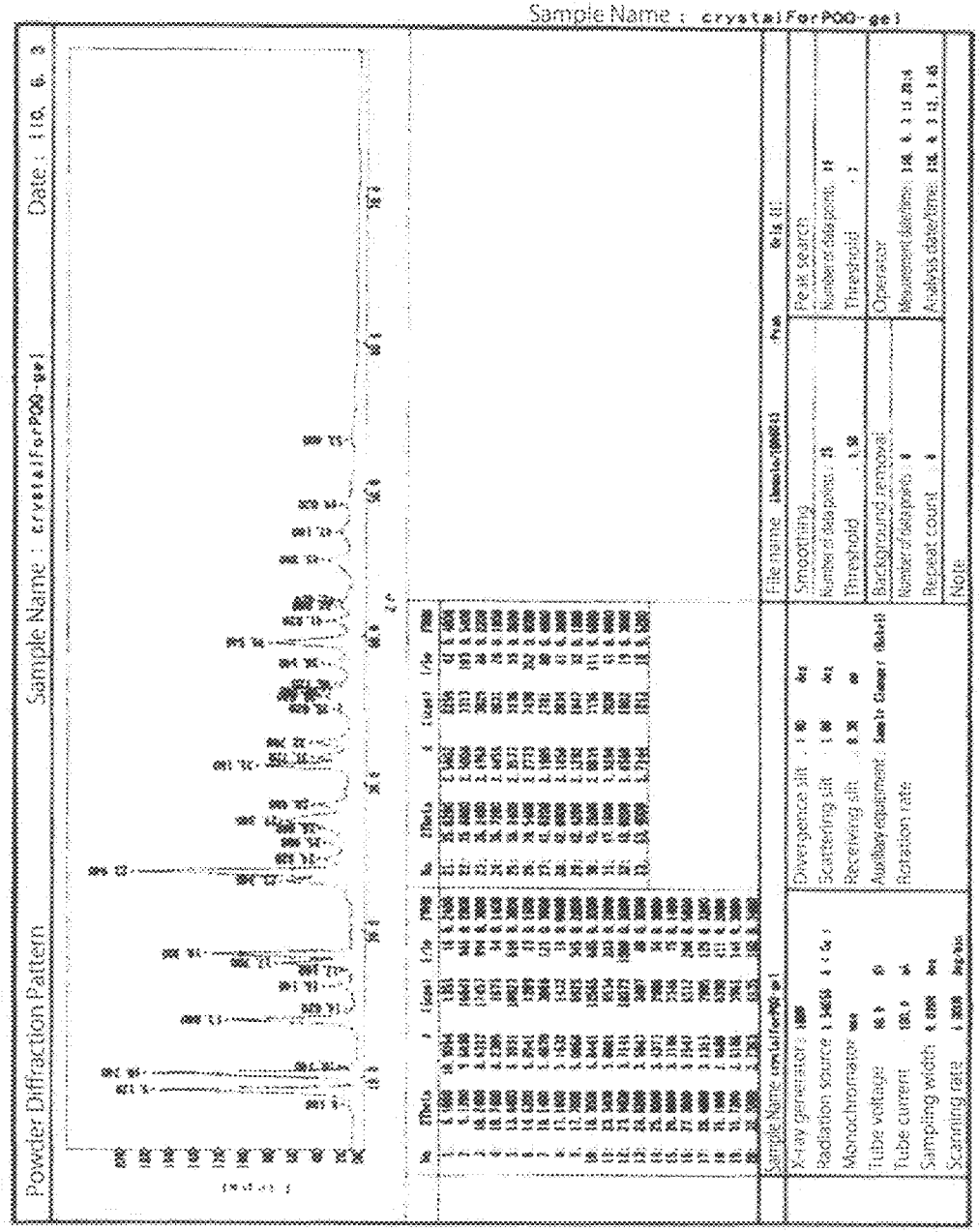
FIG. 2 shows the result of X-ray diffraction of a raw material PQQ disodium salt crystal.
Figure 3:
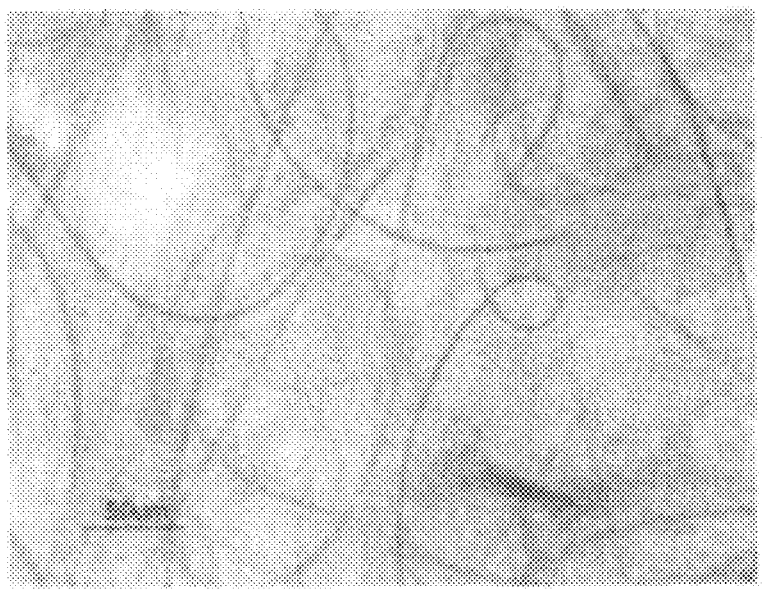
FIG. 3 shows an optical micrograph of a 1% gel.

Pyrroloquinoline quinone disodium (manufacturer: MITSUBISHI GAS CHEMICAL COMPANY, INC., powder) was used as a raw material. The result of pyrroloquinoline quinone disodium obtained by observation under an optical microscope is shown in FIG. 1. It was found that the pyrroloquinoline quinone disodium used was in a needle-like crystalline form, and shorter than that of the gelled substance (FIG. 1 and FIG. 3 below). It was also found that the pyrroloquinoline quinone disodium used was a crystalline substance, and different from the gelled substance. The result of the measurement of pyrroloquinoline quinone disodium by XRD is shown in FIG. 2. The salt was found to be in a needle-like crystalline form having a crystal structure represented by peaks at 2θ of 9.1, 10.3, and 13.8±0.4° in the powder X-ray diffraction using Cu Kα radiation.

Example 1

1% Gel

To a 15 mL plastic container for centrifugation, 0.1 g of PQQ powder of Comparative Example 1 was added, followed by the addition of 10 mL of water, and the mixture was mixed by shaking at room temperature (approximately 25° C.). This mixture was cooled in the refrigerator to 4° C., and then further mixed by shaking. When it was stored in the refrigerator overnight, the whole substance turned uniformly gel-like. The result of this gel-like substance obtained by observation under an optical microscope is shown in FIG. 3. The original needle-like substance turned into the fibrous one, which had a longer length than that of the original (FIG. 1 and FIG. 3).

Figure 4:
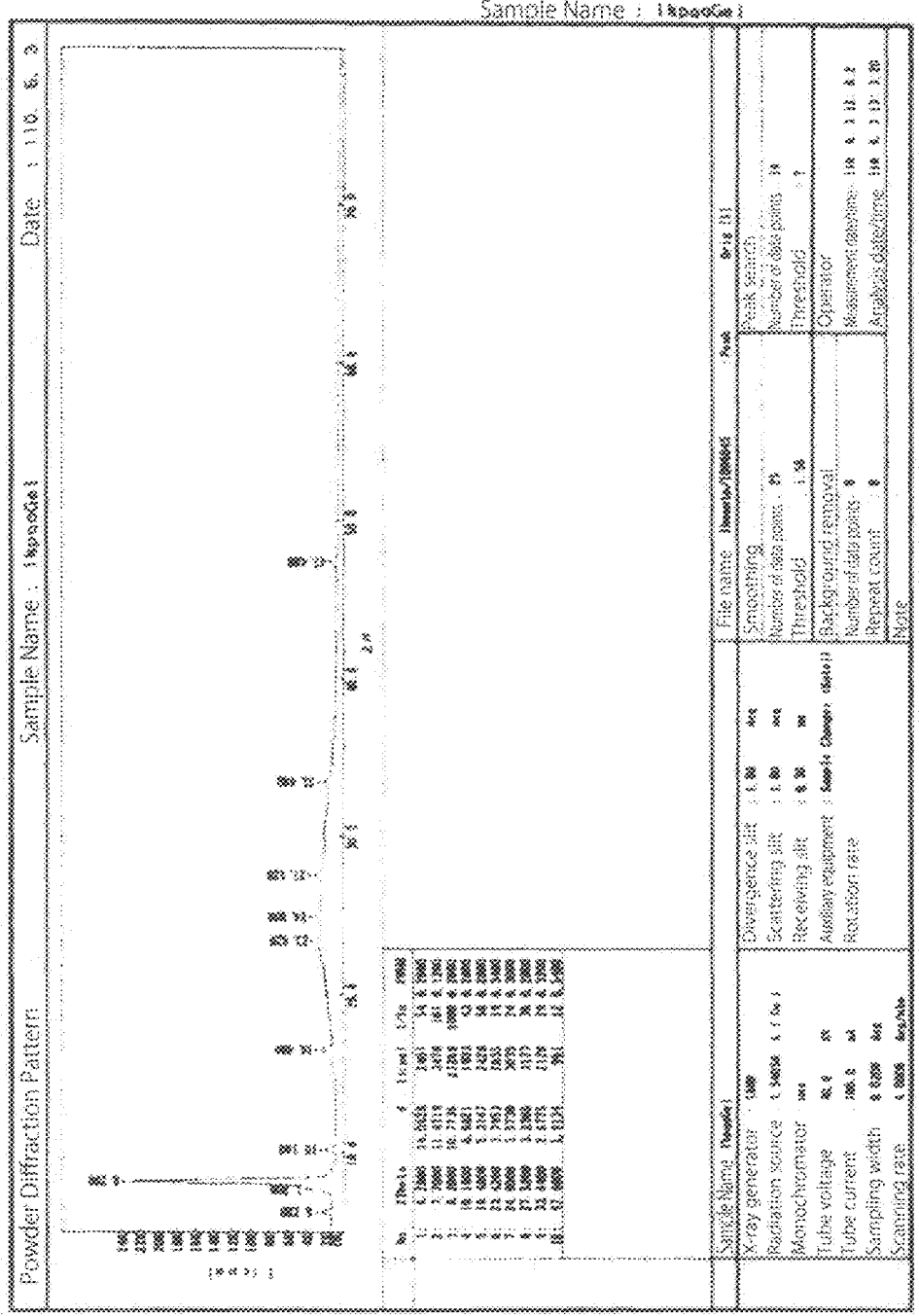
FIG. 4 shows the result of X-ray diffraction of a 1% gel.

This gel-like substance had the structure shown in FIG. 4 as measured by XRD. The strong peak is exhibited at 8.2°, and the number of diffraction peaks is decreased. From this, it is expected that the crystal structure has changed from the original structure into a structure that is close to an amorphous structure.

From these results of the analysis, it is considered that a gel capable of holding liquids was obtained because the crystal structure turned to a fibrous structure that is close to an amorphous structure during gelation. Moreover, no precipitation of solid PQQ was observed when the gel was formed, and the whole substance was in a uniform state.

Example 2

2% Gel

Figure 5:
FIG. 5 shows an optical micrograph of a 2% gel.

Similar operations to Example 1 were carried out. To a 15 mL plastic container for centrifugation, 0.2 g of PQQ powder of Comparative Example 1 was added, followed by the addition of 10 mL of water, and the mixture was mixed by shaking at room temperature (approximately 25° C.). This mixture was cooled in the refrigerator to 4° C., and then further mixed by shaking. When it was stored in the refrigerator overnight, the whole substance turned uniformly gel-like. The result of this gel-like substance observed under an optical microscope is shown in FIG. 5. Fine fibers were formed. When the concentration was increased, the fiber density was increased (FIG. 3).

Example 3

5% Gel

Figure 6:
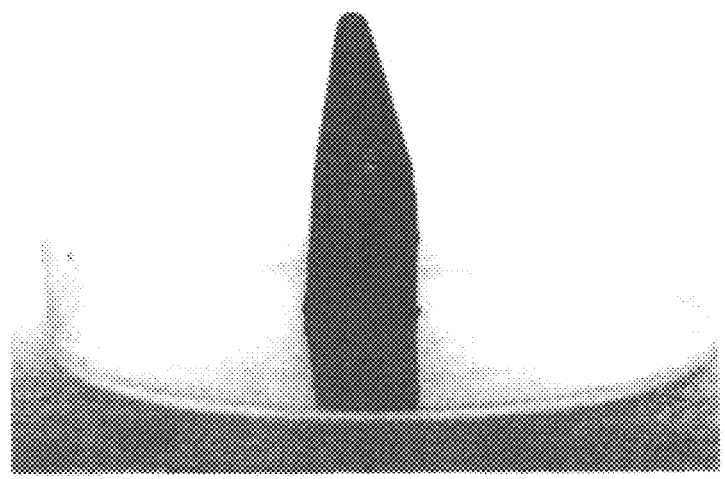
FIG. 6 shows a photograph of a molded article using a 5% gel.

Similar operations to Example 1 were carried out. To a 15 mL plastic container for centrifugation, 0.5 g of PQQ powder of Comparative Example 1 was added, followed by the addition of 10 mL of water, and the mixture was mixed by shaking at room temperature (approximately 25° C.). This mixture was cooled in the refrigerator to 4° C., and then further mixed by shaking. When it was stored in the refrigerator overnight, the whole substance turned uniformly gel-like. This substance was taken out of the container, cut to an appropriate length, put in a 9 cm petri dish, and observed. Results are shown in FIG. 6. The substance was found to have turned into a strong gel, which sustained its shape. As shown in the photograph, the entire gel was uniform, and no inside solid (PQQ) precipitate was observed.

Figure 7:
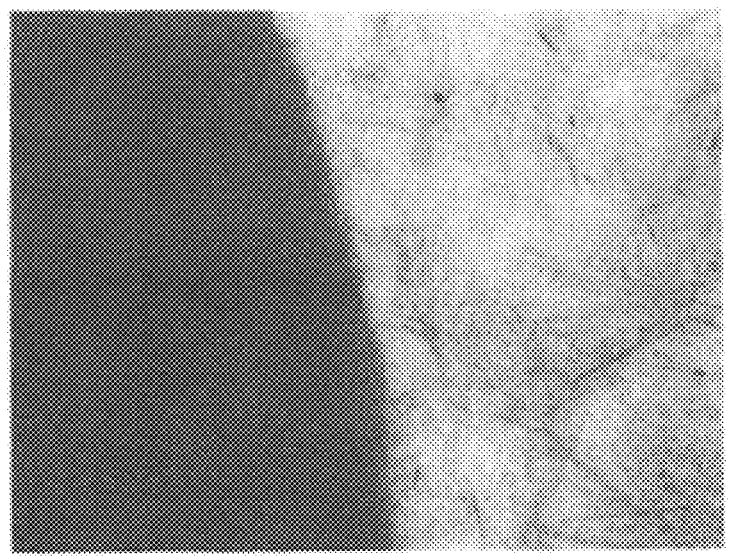
FIG. 7 shows an optical micrograph of a 5% gel.
Figure 8:
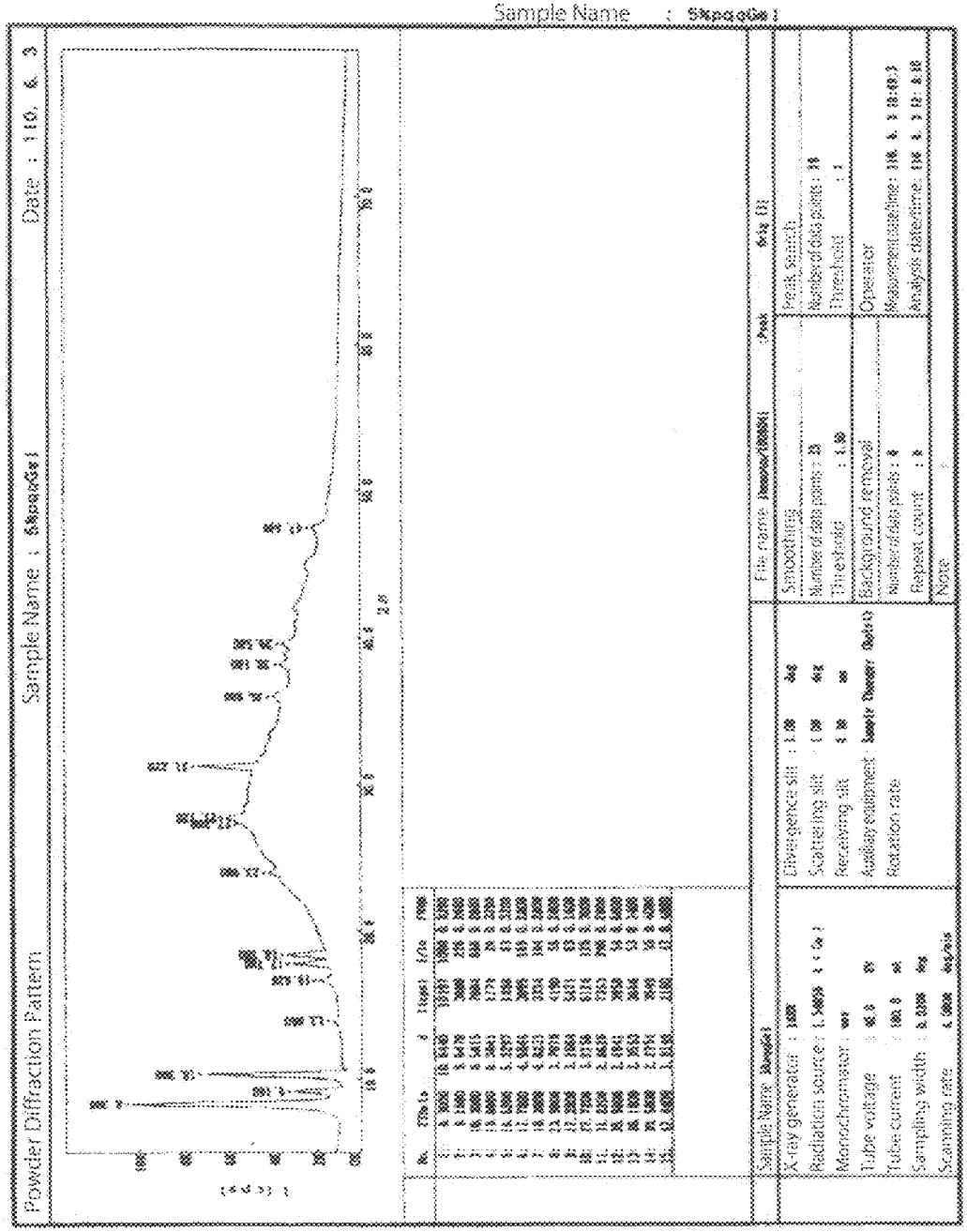
FIG. 8 shows the result of X-ray diffraction of a 5% gel.

The result of this strong gel observed under an optical microscope is shown in FIG. 7. A high density fibrous structure was observed. The result measured by XRD is shown in FIG. 8. Peaks from the original crystal structure were present together with a peak at 8.3° similar to Example 1. That is, formed is a gel composed of a mixture of a fibrous structure necessary for gel formation and the original crystal in a small amount. Under an optical microscope, the original crystalline substance was hardly observed, and therefore it is considered that the fibrous substance contains a structure that is close to the original crystal structure.

Example 4

Ethanol Gel

When dropped into a large excess of ethanol, the 5% gel prepared in Example 3 was kept in the gel state. Ethanol permeated the inside of the gel due to exchange by diffusion.

Example 5

Addition of Sweetener

When 10% of sorbitol in powder was added to the 2% gel prepared in Example 2, the gel structure was kept so that a sweetener-containing gel was formed.

Example 6 and Comparative Example 2

Dissolution Test

In Comparative Example 2, the raw material PQQ powder of Comparative Example 1 used in each Example was used. To an acrylic cell for UV measurement, 1.3 mg of the PQQ powder was added, followed by the addition of 2 mL of water.

In Example 6, to an acrylic cell for UV measurement, 27 mg of the 5% gel prepared in Example 3 (equivalent to 1.35 mg of PQQ powder) was added, followed by the addition of 2 mL of water.

The dissolution in water was monitored by absorption at 450 nm at room temperature. Absorbance measurement was performed for one hour, and the duration until the complete dissolution was calculated from the gradient of change in the concentration. The results are shown in Table 1.

TABLE 1

| Sample | | Dissolution time |
|---|---|---|
| Comparative Example 2 | Crystalline raw material | 10 minutes |
| Example 6 | 5% Gel | 13.8 hours |

These results show that gelation can suppress the dissolution rate of PQQ. This means that the PQQ gel can be expected to have an effect of inhibiting the reaction with other food components. Moreover, according to this method, the solubility can be controlled without the need for special coating technologies and substances.

Examples 7 and 8 pH Responsiveness (In Vivo Dissolution Model)

The dependence of the dissolution rate of the 5% gel on the pH was examined by the method similar to the solubility test in Example 6. Experiments were performed using a simulated gastric fluid and a simulated intestinal fluid. The results are shown in Table 2.

TABLE 2

| | Sample | Dissolution time |
|---|---|---|
| Example 7 | Simulated gastric fluid: pH 1.2, NaCl 20 g/L, HCl aq 7 mL/L | 7% dissolved in 24 hrs |
| Example 8 | Simulated intestinal fluid: pH 6.8, 0.2 mol potassium dihydrogenphosphate 250 mL/L, 0.2 mol NaOH 118 mL/L | Completely dissolved in 31 hrs |

When the simulated gastric fluid was added, the amount dissolved was not higher than was initially dissolved, and therefore the concentration in the solution did not increase. On the other hand, when the simulated intestinal fluid was added, the amount dissolved increased linearly, and the gel was immediately dissolved by stirring.

From these result, the gel of the present invention was found to be a gel having a dissolution rate that depends on the pH. Moreover, it was also found that the gel of the present invention was not dissolved in water and gastric juice, but was dissolved in the intestines. This is preferred in that because the gel is not dissolved in stomach, but dissolved in intestines in the case of oral administration, unnecessary reactions with food components can be prevented, while the gel has a characteristic of being dissolved in the intestines where absorption takes place.

Example 9

Production of Dried Product of the Gel

Figure 9:
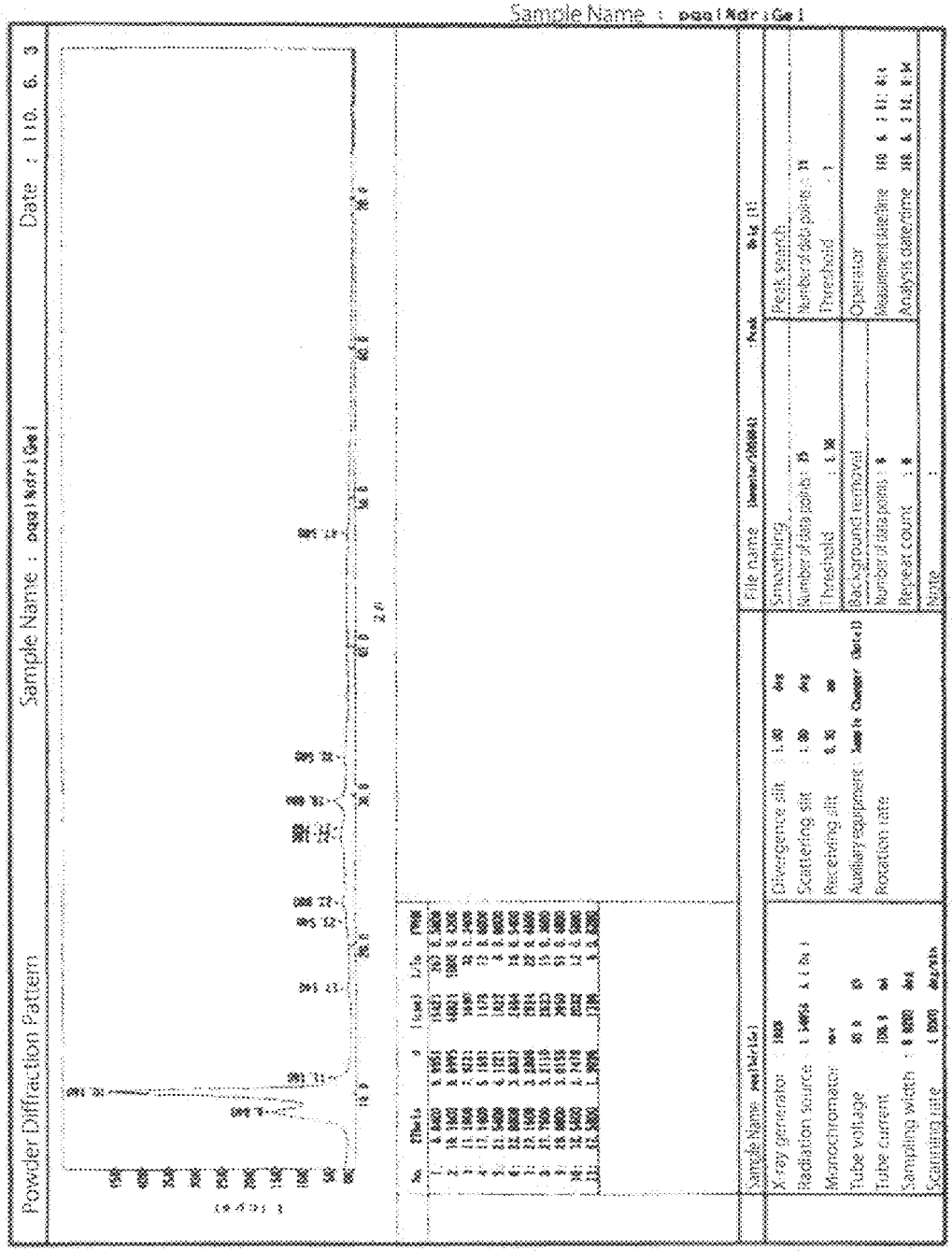
FIG. 9 shows the result of X-ray diffraction of a freeze-dried product of the gel.
Figure 10:
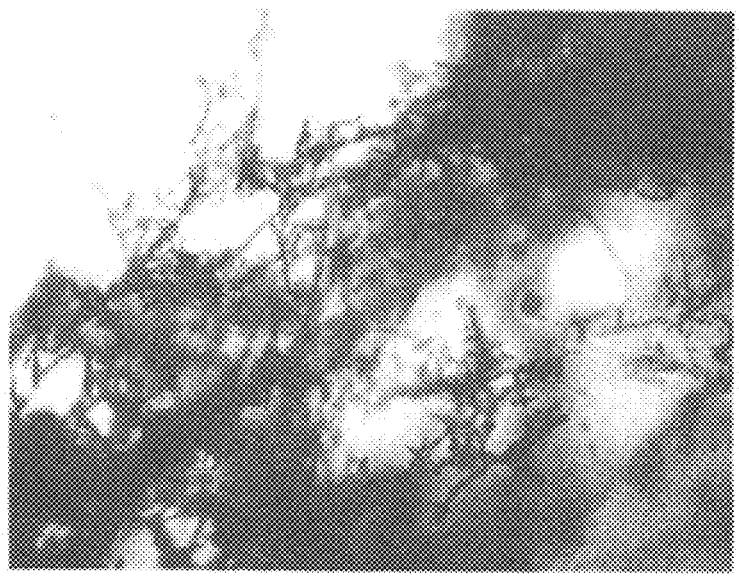
FIG. 10 shows an optical micrograph of the freeze-dried product of the gel.

The 1% gel prepared in Example 1 was frozen at 80° C. This was dried with a freeze dryer (Model: EYELA FDU2100, manufacturer: TOKYO RIKAKIKAI CO, LTD) for two days, and the pressure was eventually reduced to 8 Pa to obtain a fibrous solid. The result of this solid measured by XRD is shown in FIG. 9, and the result obtained by observation under an optical microscope in FIG. 10. The dried product of the gel was found to be a solid that held the fiber structure of the gel.

Example 10 and Comparative Example 3

Measurement of Specific Surface Area

The powder of Comparative Example 1 and the dried product of the 1% gel of Example 9 were dried at 150° C. for 20 hours as a pre-treatment using an AUTOSORB DEGASSER manufactured by Quantachrome Instruments. Using an Autosorb-6B manufactured by Quantachrome Instruments as the measurement apparatus, the specific surface area was determined by the BET method with $N_2$ adsorption.

As a result, the powder of Comparative Example 1 had a specific surface area of 2.9 $m^2/g$, while the fibrous solid of the dried product of the 1% gel of Example 9 had a specific surface area of 7 $m^2/g$.

As mentioned above, it was found that the surface area was higher when the substance became fibrous. By using the gel of the present invention, a solid with a larger surface area was produced. This can provide a fibrous solid.

Comparative Example 4

To a 15 mL plastic container for centrifugation, 0.5 g of PQQ powder of Comparative Example 1 was added, followed by the addition of 10 mL of water, and the mixture was mixed by shaking at room temperature (approximately 25° C.). After 30 minutes at room temperature, crystalline raw material precipitated in the mixed solution, yielding a non-uniform solution.

Example 12

Electron Microscope Observation

Figure 11:
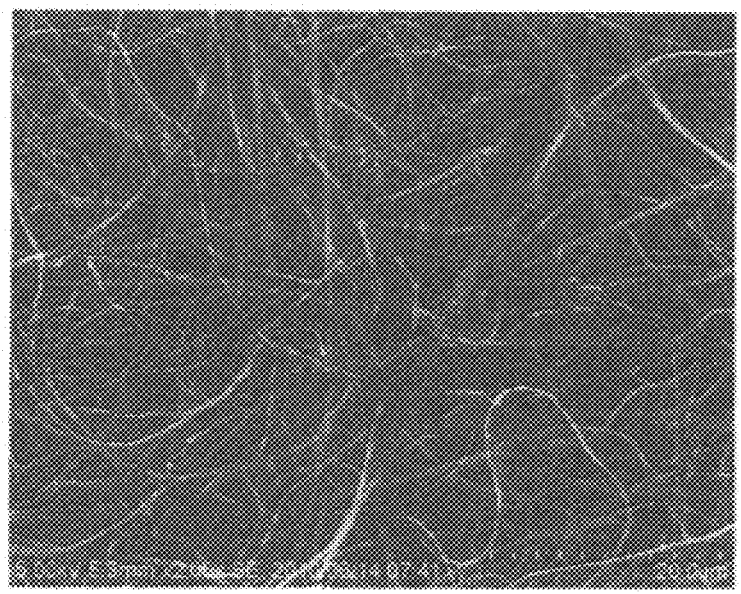
FIG. 11 shows a scanning electron micrograph of a solid obtained by drying a 1% gel after washing with ethanol.

The 1% gel prepared in Example 1 was washed with a large excess of ethanol, and cast on an aluminum foil after removal of water. This was dried at reduced pressure to obtain a non-woven PQQ. This non-woven PQQ was observed under an S-3400N scanning electron microscope manufactured by Hitachi High-Technologies Corporation. The result is shown in FIG. 11. The fiber thickness was 0.15 to 1.5 μm, and most of the fibers were fibers having a fiber thickness of 1 μm or less.

Example 13

To 10 mL of water, 0.01 g of vegetable gelatin (trade name: Agarose (low electroendosmosis), manufacturer: NACALAI TESQUE, INC.) was added, the mixture was dissolved in a microwave oven. The mixture was cooled to approximately 40° C., and 1 mL of this mixture was mixed with 1 mL of the 1% gel prepared in Example 1. The resulting mixture was cooled in the refrigerator overnight. The mixture was gelled, and fiber formation was observed under an optical microscope.

Example 14

To 10 mL of water at 75° C., 0.01 g of gelatin (trade name: Jellice, manufacturer: Nitta Gelatin Inc.) was added and dissolved. The mixture was cooled to approximately 40° C., and 0.5 mL of this mixture was mixed with 0.5 mL of the 1% gel prepared in Example 1. The resulting mixture was cooled in the refrigerator overnight. The mixture was gelled, and fiber formation was observed under an optical microscope.

Comparative Example 5

To 10 mL of water, 0.01 g of vegetable gelatin and 0.01 g of the PQQ disodium of Comparative Example 1 were added, and the resulting mixture was heated to boiling in a microwave oven. As a result, the PQQ disodium was completely dissolved. Gel formation was observed when the mixture was cooled. The result of observation under an optical microscope showed that the red PQQ layer was dispersed in a spherical form in the vegetable gelatin, and that the fiber structure disappeared. From these results, it was found that this gel resulted from gelation by the vegetable gelatin, and the PQQ was not involved in the gelation.

The invention claimed is:
1. A gel comprising a salt of pyrroloquinoline quinone, wherein said salt of pyrroloquinoline quinone is self-associated and in the form of a fibrous structure.
2. The gel of claim 1, wherein the salt is present in an amount of from 0.5 to 70% by weight based on a total weight of the gel.
3. The gel of claim 1, wherein the salt is a sodium salt of pyrroloquinoline quinone.
4. The gel of claim 1, produced by a process comprising decreasing a solubility of the salt in a mixture of the salt and a dispersion medium.
5. The gel of claim 4, wherein the decreasing is performed by decreasing a temperature of the mixture by 10° C. or more.
6. The gel of claim 4, wherein the decreasing is performed by decreasing a pH of the mixture by 0.1 or more.
7. The gel of claim 1, further comprising a sweetener.
8. The gel of claim 1, further comprising a macromolecular gelling agent.
9. A dried product of the gel of claim 1.
10. A fibrous structure, comprising a salt of pyrroloquinoline quinone.

11. A food product, comprising the gel of claim 1.

12. A pharmaceutical product, comprising the gel of claim 1.

13. A cosmetic product, comprising the gel of claim 1.

14. A gelling agent, comprising a salt of pyrroloquinoline quinone.

15. A method for producing the gel of claim 1, the method comprising:
   decreasing a solubility of the salt in a mixture of the salt and a dispersion medium.

16. The method of claim 15, wherein the decreasing is performed by decreasing a temperature of the mixture by 10° C. or more.

17. The method of claim 15, wherein the decreasing is performed by decreasing a pH of the mixture by 0.1 or more.

18. A product, comprising the dried product of claim 9,
   wherein the product is a food product, pharmaceutical product, or cosmetic product.

19. A product, comprising the fibrous structure of claim 10,
   wherein the product is a food product, pharmaceutical product, or cosmetic product.

20. The gel of claim 1, consisting of:
   said salt of pyrroloquinoline quinone, and water.

* * * * *